(12) United States Patent
Nolte

(10) Patent No.: US 8,326,644 B2
(45) Date of Patent: Dec. 4, 2012

(54) MEDICAL SYSTEM ARCHITECTURE AND METHOD FOR EXCHANGING MESSAGES

(75) Inventor: Björn Nolte, Nürnberg (DE)

(73) Assignee: Siemens Aktiengesellschaft, Munich (DE)

(*) Notice: Subject to any disclaimer, the term of this patent is extended or adjusted under 35 U.S.C. 154(b) by 2024 days.

(21) Appl. No.: 10/669,104

(22) Filed: Sep. 23, 2003

(65) Prior Publication Data

US 2004/0103169 A1 May 27, 2004

(30) Foreign Application Priority Data

Sep. 25, 2002 (DE) ................... 102 44 747

(51) Int. Cl.
G06Q 10/00 (2006.01)
G06Q 50/00 (2006.01)
G06Q 40/00 (2006.01)
(52) U.S. Cl. .................... 705/2; 705/3; 705/4
(58) Field of Classification Search ............... 705/2–4
See application file for complete search history.

(56) References Cited

U.S. PATENT DOCUMENTS

| | | | | |
|---|---|---|---|---|
| 5,513,101 A | * | 4/1996 | Pinsky et al. | 705/3 |
| 5,668,998 A | * | 9/1997 | Mason et al. | 717/104 |
| 5,671,353 A | * | 9/1997 | Tian et al. | 714/48 |
| 5,835,735 A | * | 11/1998 | Mason et al. | 710/107 |
| 5,865,745 A | * | 2/1999 | Schmitt et al. | 600/407 |
| 5,911,133 A | * | 6/1999 | Soble | 705/3 |
| 6,006,191 A | * | 12/1999 | DiRienzo | 705/2 |
| 2002/0042845 A1 | | 4/2002 | Burmann et al. | |

FOREIGN PATENT DOCUMENTS

| | | |
|---|---|---|
| DE | 199 22 793 | 12/2000 |
| WO | WO 00/50966 | 8/2000 |

OTHER PUBLICATIONS

Andriole, K., et al., Automated Examination Notification of Emergency Department Images in a Picture Archiving and Communication System, Journal of Digital Imaging: Supplement, 14, 143-144, (2001).*
"Bildgebende Systeme für die Medizinische Diagnostik," Morneburg (1995) pp. 684-696.
Mastering Regular Expressions: Power Techniques for Perl and Other Tools, Friedl (1997).

* cited by examiner

Primary Examiner — Jason Dunham
Assistant Examiner — Amber Altschul
(74) Attorney, Agent, or Firm — Schiff Hardin LLP

(57) ABSTRACT

In a medical system architecture and a message exchange method at least one modality is provided to acquire examination images, computer workstations are associated with the respective modalities to process the examination images, a device is provided to transfer data, the examination images, and messages between client applications and server applications, and a storage device is processed for the data and examination images, and further computer workstations are provided for post-processing of the data and examination images. A proxy server is associated with the data transfer device that effects a conversion of the messages between client applications and server applications according to established transformation rules. The contents of those messages are manipulated in the transfer thereof according to the aforementioned transformation rules, by a conversion routine.

11 Claims, 2 Drawing Sheets

MEDICAL SYSTEM ARCHITECTURE AND METHOD FOR EXCHANGING MESSAGES

BACKGROUND OF THE INVENTION

1. Field of the Invention

The present invention concerns a medical system architecture of the type having at least one modality to acquire examination images, computer workstations associated with the respective modalities to process the examination images, a device to transfer data, the examination images, and messages between client applications and server applications, a storage device for the data and examination images, and further computer workstations for post-processing of the data and examination images, as well as a method to exchange messages between nodes of a network.

2. Description of the Prior Art

From the book "Bildgebende Systems für die medizinische Diagnostik", published by H. Morneburg, 3rd edition, 1995, pages 684 et seq., medical system architectures, called PACS (Picture Archival and Communication Systems) are known in which image treatment stations and image processing stations (what are known as workstations) are connected with one another via an image communication network for retrieving patient data and images generated by one or more imaging modalities. The images are retrieved by experts via these workstations. DICOM (Digital Imaging and Communication in Medicine) is the industry standard for transferal of radiologic images and other medical information between computers.

In the operation of such systems, the following technical problems arise:

a) DICOM compatibility problems during network communication between DICOM nodes, both forwards, backwards and with products from other producers, must be generically resolved as well as in the context of specific architecture configurations.
   New systems must take into account how old systems (legacy systems) or other products behave. Therefore, expensive "patches" and much test expenditure are needed.

b) Maintaining anonymity of patient data and other security-relevant requirements, must be solved for specific configurations without changes in the existing DICOM products.
   The anonymity protection must be incorporated by fixed coding into the products today.

c) "DICOM Messages" from and to purchased simulators and test instruments can not be customized so as to be specific to the customer at runtime (on the fly), for example an HIS/RIS simulator can fill DICOM fields with zeros, but cannot forward empty fields, however old systems send unknown fields as empty fields.
   This is only remedied by the development of expanded simulator instruments, or special versions for test instruments.

SUMMARY OF THE INVENTION

An object of the invention is to provide a medical system architecture of the type initially described, as well as a comparable operating method, wherein an easy adaptation is achieved in a simple manner to a variety of factors and requirements dependent upon, for example, different components, which may originate from different producers.

The object is inventively achieved in a system of the type initially described wherein the device to transfer data, examination images, and messages is associated with a proxy server that effects a conversion of the messages between client applications and server applications according to predetermined transformation rules. The network detects the messages between two nodes, manipulates the content according to configurable roles, and subsequently forwards the message.

In an advantageous manner, the proxy server can operate according to the DICOM standard in the exchange of data, examination images, and messages.

Storage of the transformation rules can be inventively associated with the proxy server.

It has proven to be advantageous for the proxy server to be a separate software application.

The proxy server can inventively run on the same node or on a network node.

The object also is inventively achieved in a method of the type initially described wherein the content of the messages is manipulated in their transmission by means of a conversion routine according to transformation rules, in the exchange of the messages between client application and server application.

The applications can be DICOM applications.

It has proven to be advantageous for the transformation rules to be configurable, such that an easy adaptation to the most varied conditions and requirements can be achieved.

The conversion of messages can be inventively implemented via a proxy server that accesses stored transformation rules, so the reception, the manipulation, and the forwarding of the messages are transparent for the DICOM nodes.

DESCRIPTION OF THE PREFERRED EMBODIMENTS

Figure 1:
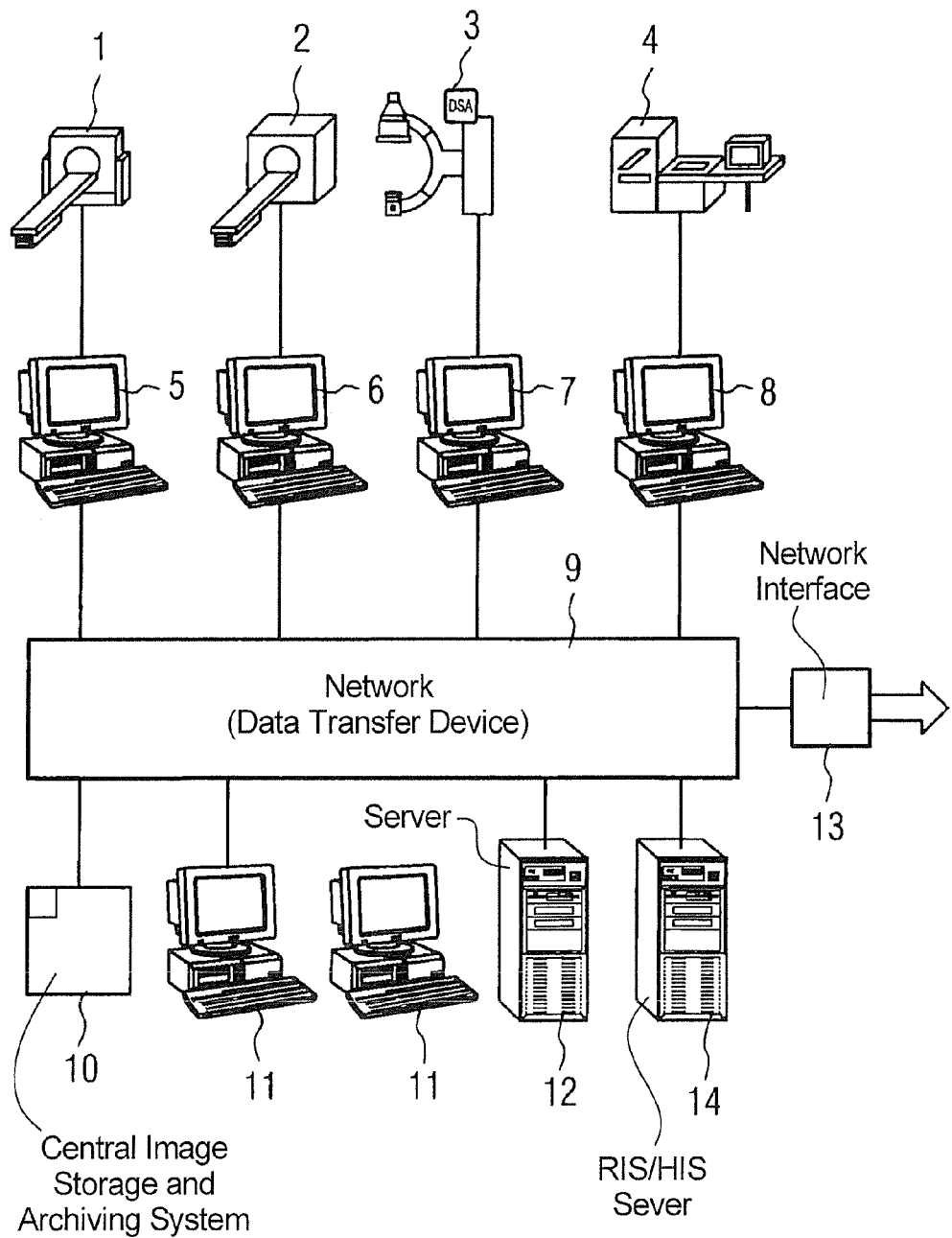
FIG. 1 is a schematic block diagram of an example of a system architecture of a hospital network.

As an example, the system architecture of a hospital network is shown in FIG. 1. The modalities 1 through 4 that, as image generating systems, serve to acquire medical images, can be, for example, a computed tomography apparatus 1, a magnetic resonance apparatus 2, a DSA apparatus 3 for digital subtraction angiography, and an x-ray unit 4 for digital radiography. Operator consoles (workstations) 5 through 8 of the modalities, with which the acquired medical images can be processed and locally stored, are connected to these modalities 1 through 4. Patient data belonging to the images is also entered via the consoles 5 through 8.

The operator consoles 5 through 8 are connected with a communication network 9 (serving as a data transfer device) formed as a LAN/WAN backbone to distribute the generated images and for communication (data and messages). For example, the images generated in the modalities 1 through 4 and the images further processed in the operator consoles 5 through 8 can be stored in central image storage systems and image archiving systems 10, or forwarded to other workstations.

Further viewing workstations 11 are connected to the communication network 9, as searching consoles that have local image storage. Such a viewing workstation 11 is, for example, a very fast minicomputer based on one or more fast processors. In the viewing workstation 11, the images that are filed in the image archiving system 10 can be subsequently called for a search and filed in the local image storage, from which they can be immediately available to the searching (reviewing) person working at the viewing workstation 11.

Furthermore, servers 12, for example patient data servers (PDS), file servers, program servers, and/or EPR servers are connected to the communication network 9.

The image exchange and data exchange over the communication network 9 ensue according to DICOM standard, an industry standard to transfer images and further medical information between computers, with which a digital communication between diagnosis devices and therapy devices of different producers is possible. A network interface 13 can be connected to the communication network 9, via which the internal communication network 9 is connected with a global data network, for example the World Wide Web, such that the standardized data can be exchanged worldwide with different networks.

An RIS server and/or a KIS server 14 can be connected to the communication network 9, with which the operator consoles 5 through 8 communicate by means of the communication network 9 via TCP/IP protocols.

Figure 2:
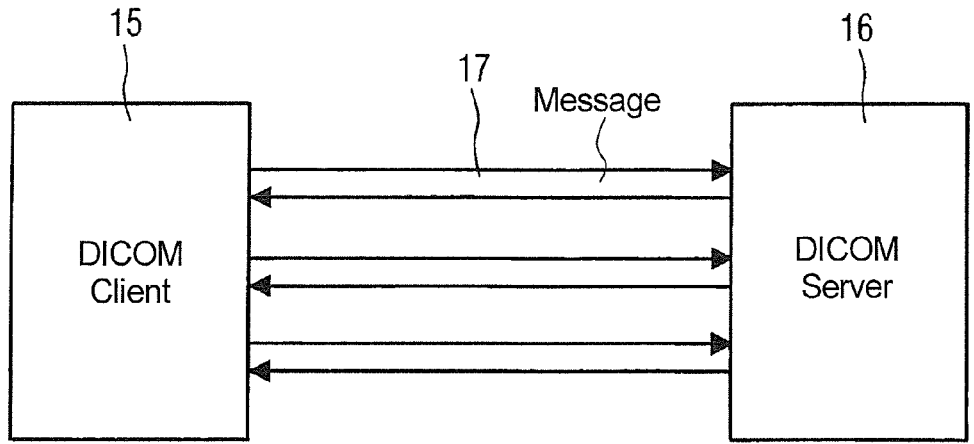
FIG. 2 schematically illustrates a known communication between a DICOM client application and a DICOM server application.

FIG. 2, a conventional communication between an application 15 on a DICOM client (for example on one of the modalities 1 through 4) and an application 16 on a DICOM server (for example on the server 14) is schematically shown. In a first connection, a number of messages 17 are exchanged that proceed directly from the DICOM client to the DICOM server and back.

Figure 3:
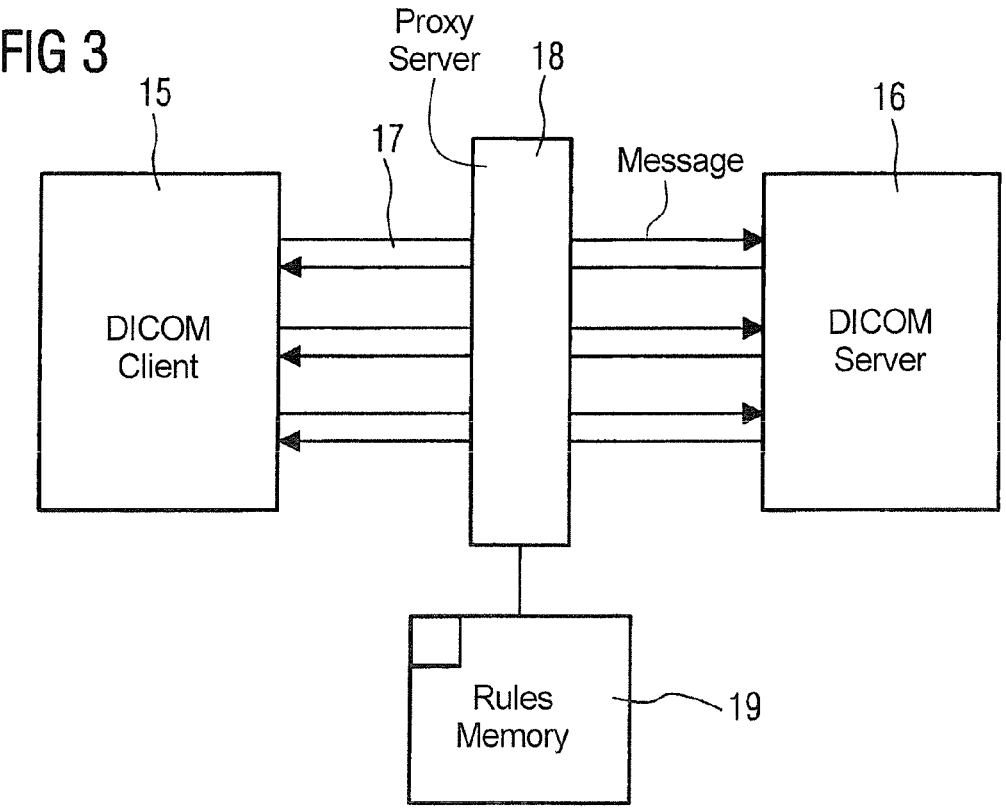
FIG. 3 schematically illustrates the inventive communication between a DICOM client application and a DICOM server application.

FIG. 3 shows an inventive communication between a client application 15 and a server application 16. The messages 17 from the DICOM client to the DICOM server and back are first supplied to a proxy server 18 that converts them with transformation rules stored in a memory 19.

The proxy server 18 is a component that administers the data traffic in the internet for a local network (LAN).

This proxy server 18 can be a separate software application. It can run on the same node or on a network node. It is rule-based and can be configured very dynamically. It is semantic-free.

The data in the communication network 9, the content of which is manipulated according to configurable rules, is acquired between the DICOM nodes by the proxy server 18 and subsequently forwarded to the receiver. The receipt, the manipulation, and the forwarding is totally transparent for the DICOM nodes, analogous to an HTTP proxy.

The manipulation is highly robust due to the use of the powerful "Regular Expression Pattern Matching" algorithm, that originates from the mathematician S. Kleene and, for example, is specified in the book "Mastering Regular Expressions. Powerful techniques for Perl and other tools" by Jeffrey E. F. Friedl. It is used in order to specify samples of strings clearly and with a strong algebraic basis. The "Regular Expression" samples are factored out in configuration files. No transmission of the source codes is necessary in order to reprogram the proxy.

The medical system architecture according to the invention is distinguished itself by the following developments:
- Transparent proxy between an older generation of DICOM-based products and a new product.
- Transparent proxy between DICOM products of various producers or interpretations.
- Security firewall to other networks or DICOM nodes.
- Expansion of DICOM simulators or interoperability test instruments.

Abbreviations used in the specification:

| | |
|---|---|
| DICOM | Digital Imaging and Communications in Medicine<br>DICOM standard is an industry standard to transmit images and further medical information between computers to enable the digital communication between diagnosis devices and therapy devices of different producers. |
| EPR | Electronic Patient Record<br>(Electronic Patient File) |
| HIS<br>(KIS) | Hospital Information System<br>(Krankenhaus Information System):<br>System for general hospital management, with the main features of patient management, bookkeeping, accountancy, personal management and so forth. |
| HTTP | Hypertext Transfer Protocol<br>defines the access of clients (for example web browsers) to information-stored server-side on the World Wide Web. HTTP defines how messages are formatted and transferred, and which actions web server and web browser should implement as reply to various instructions. |
| LAN | Local Area Network<br>A local network that comprises a group of computers and other devices, that are distributed over a relatively limited area and connected via communication lines, that enable the interaction of every device with every other device in the network. |
| PACS | Picture Archival and Communication System:<br>computer-aided image information systems to optimize patient care, operating sequence in the radiological department, image distribution in the hospital, image supply for research and teaching, and image archiving. |
| RIFS | (Radiology Information System):<br>Information system for data management within the radiology department, that, for example, aids patient admission, the creation of work lists, reporting, report management, bookkeeping, and accounting, and so forth. |
| TCP/IP | Transmission Control Protocol/Internet Protocol<br>The protocol for the communication between computers is integrated into the operating system UNIX and is a de facto standard for data transmission over networks, including the Internet. |
| WAN | Wide Area Network<br>A communication network to connect regions geographically very separate. A wide area network can comprise a plurality of local networks. An example for a wide area network is the Internet. |

Exemplary Example Code For A Tool For Converting From An ASCII Based File Using The Minimal Language (Set-Content-From-String, Set-Content-From-File, Open-Item, Close-Item) With Some Cosmetic Extensions

Exemplary Example Code For A Tool For Converting From An ASCII Based File Using The Minimal Language (Set-Content-From-String, Set-Content-From-File, Open-Item, Close-Item) With Some Cosmetic Extensions

```
include <stdio.h> include <string.h>

//    include some-dicom-toolkit-header-files
```

// for dicom stream build and dicom constrains checking

// ----------------------------------------------------------------------------

// Globals define BIGSTRSIZE 1000 define BIGPNAMESIZE 500 define BUFFERSIZE 1024*1024*10 define VRSIZE 3 define SET_FROM_STR 's' define SET_FROM_FUN 'f' define OPEN_ITEM 'O' define CLOSE_ITEM 'C' define TOOLKIT_DUMP 'D' define DEBUGTOGGLE '!' define COMMENT_BEGIN '#' define QUIT 'q'

// Toolkit data structures should be added here

```
char       appName[10] = "foobar";
char*      fileName;
int lineNo = 0; // line number in input command file typedef struct line _t
{
    int cmd;
    unsigned long tag;
    char value[BIGSTRSIZE];
    unsigned long slot1;            // DICOM group value
```

```
        char slot2[BIGPNAMESIZE];    // DICOM private tag: OwnerCode
        unsigned long slot3;         // DICOM element value or DICOM
                private tag: ElementByte
        char slot4[VRSIZE];          // DICOM private tag: value rep-
        resentation
} line_t;

line_t line;

char callbackdata = 0x1;

//    Stack for message id
        #define STACKMAXVAL 10000
        int msgId_sp=0;
int msgId_val[STACKMAXVAL];

//    ------------------------------------------------------------------------
------
//    Functions
        void pushmsgId(int v){
                if (msgId_sp < STACKMAXVAL)
                        msgId_val[msgId_sp++] = v;
                else
                        fprintf(stderr, "Schematic-example-code at cmdline %d:
                                Stack overflow\n",lineNo);
}
        int popmsgId(void){
                if (msgId_sp>0)
                        return msgId_val[--msgId_sp];
```

```
        else {
            fprintf(stderr, "Schematic-example-code at cmdline %d:
                Stack underflow\n",lineNo);
            return 0;
        }
    } void ErrExit(char * errMsg, int errNum)
    {
        if (errNum == NORMAL_COMPLETION) {
            fprintf(stderr, "Schematic-example-code at cmdline %d:
                %s\n", lineNo, errMsg);
        } else {
            fprintf(stderr, "Schematic-example-code at cmdline %d: %s
                with TOOLKIT error %s\n", lineNo, errMsg, Er-
                ror-Message( (STATUS) errNum));
        }
        status = Release_Application( &appID);
        exit(-1);
    } static STATUS simpleCallBack (
                int         msgID,
                unsigned long   tag,
                int         firstCall,
                void*       userInfo,
                int*        dataLen,
                void**      dataBuffer,
```

```
                    int*           isLast)
{
    static char  buffer[BUFFERSIZE];
    size_t       byte_pos;
    FILE *stream;
    char errMsg[100];
int ch;

*isLast = 1;

if( (stream = fopen( line.value, "rb" )) == NULL )  {
        sprintf( errMsg, "Failed to open file: '%s'\n",
            line.value );
        ErrExit(errMsg,NORMAL_COMPLETION);
}
    byte_pos = 0;
ch = fgetc( stream );
    while ( feof( stream ) == 0 )  {
        buffer[byte_pos] = ch;
        ch = fgetc( stream );
        byte_pos++;
    }
    //    byte_pos points one ahead of last filled pos in buffer
         and equals number of bytes
    if( fclose ( stream ) )  {
        sprintf( errMsg,"Failed to close file: '%s'\n",
            line.value );
```

```
                    ErrExit(errMsg,NORMAL_COMPLETION);
    }

//      if odd number of bytes report error
        if ((byte_pos % 2) == 1)  {
                ErrExit("Odd number of bytes
                        read.\n",NORMAL_COMPLETION);
    }

*dataBuffer = buffer;
    *dataLen = (int)byte_pos;

return NORMAL_COMPLETION;
}

VR str2vr(char * str)
{ if ((str[0] == 'A') && (str[1] == 'E')) {return AE;}
        if ((str[0] == 'A') && (str[1] == 'S')) {return AS;}
        if ((str[0] == 'C') && (str[1] == 'S')) {return CS;}
        if ((str[0] == 'D') && (str[1] == 'A')) {return DA;}
        if ((str[0] == 'D') && (str[1] == 'S')) {return DS;}
        if ((str[0] == 'D') && (str[1] == 'T')) {return DT;}
        if ((str[0] == 'I') && (str[1] == 'S')) {return IS;}
        if ((str[0] == 'L') && (str[1] == 'O')) {return LO;}
        if ((str[0] == 'L') && (str[1] == 'T')) {return LT;}
        if ((str[0] == 'P') && (str[1] == 'N')) {return PN;}
        if ((str[0] == 'S') && (str[1] == 'H')) {return SH;}
        if ((str[0] == 'S') && (str[1] == 'T')) {return ST;}
        if ((str[0] == 'T') && (str[1] == 'M')) {return TM;}
```

```
        if ((str[0] == 'U') && (str[1] == 'T')) {return UT;}
        if ((str[0] == 'U') && (str[1] == 'I')) {return UI;}
        if ((str[0] == 'S') && (str[1] == 'S')) {return SS;}
        if ((str[0] == 'U') && (str[1] == 'S')) {return US;}
        if ((str[0] == 'A') && (str[1] == 'T')) {return AT;}
        if ((str[0] == 'S') && (str[1] == 'L')) {return SL;}
        if ((str[0] == 'U') && (str[1] == 'L')) {return UL;}
        if ((str[0] == 'F') && (str[1] == 'L')) {return FL;}
        if ((str[0] == 'F') && (str[1] == 'D')) {return FD;}
        if ((str[0] == 'O') && (str[1] == 'B')) {return OB;}
        if ((str[0] == 'O') && (str[1] == 'W')) {return OW;}
        if ((str[0] == 'O') && (str[1] == 'L')) {return OL;}
        if ((str[0] == 'S') && (str[1] == 'Q')) {return SQ}
        return UNKNOWN_VR;
} void trim_rest_of_line(void)
{
int c;

c = getchar() ;
    while (c !_ '\n')  {
        if (c == EOF)  {
        return;
        }
    c = getchar();
    }
}
```

```c
void trim(void)
{
int c;

c = getchar();
    while ((c == ' ') ||
        (c == '\t'))  {
        c = getchar();
} ungetc(c,stdin);
} int parseLine(line_t *line)
{
        enum{CMD, TAG, VALUE} state = CMD;
        int  c, i;
char tagAsStr[BIGSTRSIZE];
// clear return data
        line->cmd = 0;
line->tag = 0;
        for(i=0; i < BIGSTRSIZE; i++)  {
                { line->value[i] = '\0';
}
        line->slot1 = 0;
line->slot3 = 0;
        for(i=0; i < BIGPNAMESIZE; i++)  {
```

```
            line->slot2[i] = '\0';
    } for(i=0; i < VRSIZE; i++) {
        line->slot4[i] = '\0';
    } for(i=0; i<BIGSTRSIZE; i++) {
        tagAsStr[i] = '\0';
    } trim();

// get the command c = getchar();
line->cmd = c;

if ((c == EOF) || (c == QUIT)) {
        return EOF;
    } if (c == COMMENT_BEGIN) {
        trim_rest_of_line ();
        return COMMENT_BEGIN;
    } if (c == TOOLKIT_DUMP) {
        trim_rest_of_line ();
        return TOOLKIT_DUMP;
    } if (c == DEBUGTOGGLE) {
```

```
            trim_rest_of_line ();
            return DEBUGTOGGLE;
    } if (!((c == SET FROM STR) ||
            (c == SET_FROM_FUN) ||
            (c == TOOLKIT_ DUMP) ||
            (c == OPEN_ITEM) ||
            (c == CLOSE_ITEM)))   {
            ErrExit ("Failed to parse line, unexpected
                    cmd\n",NORMAL_COMPLETION);
    }
    trim();

// get the first slot of the tag.
        // Tag format:
        //      (0008,0090)
//      (0009,SIEMENS CM VA0 CMS,11)

if ((c = getchar()) != ' (')   {
            ErrExit("Failed to parse line, tag must begin with a
                    parantesis\n",NORMAL_COMPLETION);
    }
        for(i=0; i<4; i++)   {
            c = getchar();
            if (((c >= '0') && (c <= '9')) ||
                ((c >= 'A') && (c <= 'F')))
            {
```

```
            tagAsStr[i] = c;
        } else
        {
            ErrExit("Failed to parse line, invalid
                tag\n", NORMAL_COMPLETION);
        }
    } if (sscanf(tagAsStr,"%X",&line->slotl) != 1)  {
        ErrExit("sscanf failed\n",NORMAL_COMPLETION);
    } for (i=0; i<BIGSTRSIZE; i++)  {
        tagAsStr[i] = '\0';
    } if ((c = getchar()) != ',')  {
        ErrExit("Failed to parse line, missing comma after group
            element in tag\n",NORMAL_COMPLETION);
    }

/ / get the second slot
    / / if a comma follows its private if endparantesis it's a
    normal tag, else error c = getchar();
    i = 0;
    while (!((c (c == ',') | |
        ((c == ')')))  {
        if ((c == '\n') | |
```

```
            (c == EOF)) {
                ErrExit ("Failed to parse line, unexpected end in
                    tag\n", NORMAL_COMPLETION);
            }
            tagAsStr[i++] = c;
            c = getchar();
        }
        if (c == ')') { / / nonprivate tag
            for(i=0; i<4; i++)
                if (!(((tagAsStr[i] >= '0') && (tagAsStr[i] <= '9'))
                    ||
                    ((tagAsStr[i] >= 'A') && (tagAsStr[i] <= 'F')))) {
                    ErrExit("Failed to parse line, invalid hex value in sec-
                        ond part of nonprivate tag\n",NORMAL_COMPLETION);
                }
            }
            if (sscanf (tagAsStr, "%X", &line->slot3) != 1) {
                ErrExit ("sscanf failed, expected hex as second and
                    last part of tag\n", NORMAL_COMPLETION);
            }
        } else { / / private tag
            strcpy (line->slot2,tagAsStr);
            if (c != ',') {
                ErrExit ("Failed to parse line, comma after slot2 miss-
                    ing in private tag\n", NORMAL_COMPLETION);
```

```
        }
                for(i=0; i<BIGSTRSIZE; i++) {
                        tagAsStr[i] = '\0';
        }

// slot3
                c = getchar();
                i = 0;
        while (c != ',') {
                        if ((c == '\n') ||
                        (c == EOF))  {
                ErrExit("Failed to parse line, unexpected end in slot3
                        in private tag\n",NORMAL_COMPLETION);
                }
                tagAsStr[i++] = c;
                c = getchar () ;
        }

// slot4
                line->slot4[0] = getchar();
line->slot4[1] = getchar();
                if ((c = getchar()) != ')') {
                ErrExit("Failed to parse line, missing ending parante-
                        sis in private tag\n",NORMAL_COMPLETION);
        }
                if (sscanf(tagAsStr,"%X",&line->slot3) != 1) {
                ErrExit("sscanf failed\n",NORMAL_COMPLETION);
```

```
        }
    } if ((line->cmd == SET_FROM_STR) || (line->cmd ==
        SET_FROM_FUN))
    {
        c = getchar();
        if (!((c =_' ') || (c == '\t')))
        {
            ErrExit("Failed to parse line, delimiter before value
                    not space or tab\n", NORMAL_COMPLETION);
        }
    }
    else
    {
        trim();
    }

// get the value
    c = getchar();
    i = 0;
    while (! ( (c == EOF) ||
                (c == '\n')))   {
        line->value[i++] = c;
        c = getchar();
    } return c; // EOF or '\n'
}
```

```
int
main (int argc, char * argv[])
{
    int outer_msgId;
    bool debugging = FALSE;
    if (argc != 2)
    {
        fprintf(stderr, "\nSchematic-example-code Usage:  Sche-
            matic-example-code filename < commands\n\n");
        fprintf(stderr, "List of commands:\n\n");
        fprintf(stderr, "\t's' for SET_FROM_STR \n");
        fprintf(stderr, "\t'f' for SET_ FROM_ FUN \n");
        fprintf(stderr, "\t'o' for OPEN_ITEM \n");
        fprintf(stderr, "\t'C' for CLOSE_ITEM \n");
        fprintf(stderr, "\t'D' for TOOLKIT_DUMP \n");
        fprintf(stderr, "\t'!' for DEBUGTOGGLE \n");
        fprintf(stderr, "\t'#' for COMMENT_BEGIN \n");
        fprintf(stderr, "\t'q' for QUIT \n");
        return -1;
    }
fileName = argv[l];
    status = Library_Initialization(NULL, NULL, NULL);
    if (status != NORMAL_COMPLETION)
    ErrExit ("Library_Initialization", status);
    status = Register_Application(&appID, appName);
```

```
        if (status != NORMAL_COMPLETION)
        ErrExit ("Register_Application", status);

//status = Create_ File (&msgId, fileName, "DICOMDIR",
                C_STORE_RQ);
        status = Create_Empty_File (&msgId, fileName);
        if (status != NORMAL_COMPLETION)
        ErrExit("Create_File", status);

top_msgId = msgId;

while (parseLine(&line) != EOF)  { lineNo++;

if ((line.cmd == QUIT) ||
            (line.cmd == COMMENT_BEGIN) ||
            (line.cmd == DEBUGTOGGLE) ||
        (line.cmd == EOF))  { if (debugging)  {
            fprintf(stdout, "Schematic-example-code at cmdline %d:
                parsed cmd = \"%c\" OK!\n", lineNo, line.cmd);

}
    }    else { if (line.slot2[0] __ '\0')  { if (debugging)  {
            fprintf(stdout, "Schematic-example-code at cmdline %d:
                parsed cmd = \"%c\" tag = (%4X,%4X) value \"%s\"
                OK!\n",
                lineNo,line.cmd,line.slotl,line.slot3,line.value);
```

```
        } line.tag = (line.slotl << 16) + line.slot3;

}   else { if (debugging)  { fprintf(stdout, "Schematic-example-code at cmdline %d:
                            parsed cmd =        \"%c\" tag =   (%4X, %s, %4X, %s) value
                    \"%s\" OK!\n", lineNo,line.cmd,line.slotl,line.slot2,line.slot3,li
                            ne.slot4,line.value,lineNo);

}
                }
        } switch (line.cmd)  { case SET_FROM_STR:

if (line.slot2[0] == '\0')    //  standard tag
                    {
                    if (strcmp(line.value,  "") == 0)
                            {
                    status = Set_Next_Value_To_NULL(msgld, line.tag);
                            if (status == INCOMPATIBLE_VR)
                            {
                                    status = Set_Next_Value_From_String(msgld,
                                    line.tag, ""_;
                            }
                            }
```

```
          else
          {
              status = Set_Next_Value_From_String(msgId, line.tag,
                   line.value);
          }
      if ((status != NORMAL_COMPLETION) && (status !=
              INVALID_CHARS_IN_VALUE) && (status !=
              INVALID_VALUE_FOR_VR))
      ErrExit("Set_Next_Value_From_String", status);

}
          else                       // private tag
  {
      unsigned long aValLength;
      status = Get_pValue_Length(msgId,
                  line.slot2,
                  (unsigned short) line.slot1,
                  (unsigned char) line.slot3,
                  1,
                  &aValLength);
          if ((status == NULL_VALUE) || (status ==
          EMPTY_VALUE))
              {
                  status = NORMAL_COMPLETION;
  }
          if (!((status == NORMAL_COMPLETION) ||
                  (status == INVALID_PRIVATE_CODE) ||
```

```
            (status == INVALID_TAG)))  {

ErrExit("Get_pValue_Length", status);

}

// CASE no owner element; no data element:

if (status == INVALID_PRIVATE_CODE)  { status = Add_Private_Block(msgId,line.slot2,(unsigned char)line.slot1);

if (status == NORMAL_COMPLETION)  { status = Add_Private_Attribute(msgId,line.slot2, (unsigned short)line.slot1, (unsigned char)line.slot3, str2vr(line.slot4));

if (status != NORMAL_COMPLETION)  {

ErrExit("Add_Private_Attribute failed", status); }

}

}  else  {

ErrExit("Add_Private_Block failed", status);

}

}       else if (status == INVALID_TAG)  {

// CASE owner element exist; no data element:  do 2.

status = Add_Private_Attribute(msgId,line.slot2, (unsigned short)line.slot1, (unsigned char)line.slot3, str2vr(line.slot4));

if (status != NORMAL_COMPLETION)  {

ErrExit("Add_Private_Attribute\n", status);
```

```
        }
    } else if (status == NORMAL_COMPLETION) {

// CASE owner element exist; data element exist: do 3.

status = Set_pValue_Representation(msgId,line.slot2,
                            (unsigned short)line.slot2,
                            (unsigned char)line.slot3,
                            str2vr(line.slot4));
        if (!((status ==NORMAL_COMPLETION) ||
                (status == VR_ALREADY_VALID))) {
            ErrExit("Set_pValue_Representation", status);
        }
    } else {
        ErrExit("Other error while doing private attribute",
            status);
    }
    // We have possibly built a private structure, now set
        the private value
        if (strcmp(line.value, "") == 0)
        {
        status = Set_Next_pValue_To_NULL(msgId,
                    line.slot2,
                    (unsigned short)line.slot1,
                    (unsigned char)line.slot3);
            if (status == INCOMPATIBLE_VR)
            {
        status = Set_Next_pValue_From_String(msgId,
```

```
                    line.slot2, (unsigned short)line.slot1, (unsigned char)line.slot3),

"");

}
        }
        else
        {
            status = Set_Next_pValue_From_String(msgId, line.slot2, (unsigned short)line.slot1, (unsigned char)line.slot3, line.value);
        }
        if ((status != NORMAL_COMPLETION) && (status !=
                INVALID_CHARS_IN_VALUE) && (status !=
                INVALID_VALUE_FOR_VR))
        {
            ErrExit("Set_Next_pValue_From_String", status); }
        }
    }
break;

case SET_FROM_FUN:

if (line.slot2[0] == '\0') { // standard tag status = Set_Value_From_Function(msgId, line.tag, NULL, simpleCallBack);
```

```
        if (status != NORMAL_COMPLETION)
            ErrExit("Set_Value_From_Function", status);
    } else {
        unsigned long aValLength;
        status = Get_pValue_Length(msgId,
                        line.slot2,
                        (unsigned short) line.slot1,
                        (unsigned char) line.slot3,
                        1,
                        &aValLength);
        if (!((status == NORMAL_COMPLETION) ||
                    (status == INVALID_PRIVATE_CODE) ||
                    (status == INVALID_TAG)))  {
            ErrExit("Get_pValue_Length", status);
        }
    }

// CASE no owner element; no data element:
        if (status == INVALID PRIVATE CODE)  {
            status = Add_Private Block(msgId,line.slot2, (unsigned
                    char)line.slot1);
            if (status == NORMAL_COMPLETION)  {
                    status = Add_Private_Attribute(msgId,line.slot2,
                            (unsigned short)line.slot1,
                            (unsigned char)line.slot3,
                            str2vr(line.slot4));
                    if (status != NORMAL_COMPLETION)  {
                            ErrExit("Add_Private_Attribute failed", status);
```

```
                    }
            }       else {
                    ErrExit("Add_Private_Block failed", status);
            }
    } else if (status == INVALID_TAG) {

// CASE owner element exist; no data element: do 2.
            status = Add_Private_Attribute(msgId,line.slot2,
                            (unsigned short)line.slot1,
                            (unsigned char)line.slot3,
                            str2vr(line.slot4));
            if (status != NORMAL_COMPLETION) {
                    ErrExit("Add_Private_Attribute\n", status);
            }
    }       else if (status == NORMAL_COMPLETION) {

// CASE owner element exist; data element exist: do 3.
            status = Set_pValue_Representation(msgId,line.slot2,
                            (unsigned short)line.slot1,
                            (unsigned char)line.slot3,
                            str2vr(line.slot4));
            if (!((status == NORMAL_COMPLETION) ||
                    (status == VR_ALREADY_VALID))) {
                    ErrExit("Set_pValue_Representation", status);
            }
    }       else {
            ErrExit("Other error while doing private attribute",
                    status);
```

```
}
    // We have possibly built a private structure, now set
        the private value
    if ((status = Set_pValu_From_Function(msgId,
                line.slot2,
                (unsigned short)line.slot1,
                (unsigned char)line.slot3,
                NULL,
                simpleCallBack)) !=
            NORMAL_COMPLETION) {
        ErrExit("Set_pValue_From_Function", status);
    }
        }
break;

case CLOSE_ITEM:
        outer_msgId = popmsgId();
        Set_Next_Value_From_Int(outer_msgId, line.tag, msgId);
        msgId= outer_msgId;
        if (status != NORMAL_COMPLETION)
ErrExit("Set_Value_from_int", status);
break;

case TOOLKIT_DUMP:
List_File(msgId, NULL);
if (status != NORMAL_COMPLETION)
        ErrExit("List_File", status);
        break;
```

```
case OPEN_ITEM:

pushmsgld(msgld);

status = Open_Item(&msgld, line.value);

if (status != NORMAL_COMPLETION)

ErrExit("Open_Item", status);

break;

case COMMENT_BEGIN:

// do nothing for comments break;

case DEBUGTOGGLE:

if (debugging) { debugging = FALSE;

} else { debugging = TRUE;

} break;

default:

fprintf(stderr, "Schematic-example-code at cmdline %d:

\"%c\": ",lineNo,line.cmd);

ErrExit("Unexpected value",NORMAL_COMPLETION);

break;

}

} if (debugging) { fprintf(stdout, "Schematic-example-code:  Writing dicom output to:  %s\n", fileName);
```

```
}
        long aStatus = UNDEFINED;
        TransferSyntax aSyntax;
        const int aBufferSize = 128;
char aBuffer[aBufferSize];
        status = Get_Value_To_String(msgId, 0x00020010, aBuffer-
                Size, aBuffer);
        if (status == NORMAL_COMPLETION)
        {
                aSyntax.setFromUidString(aBuffer);
        }
        else
        {
                status = File_To_Message(msgId);
                if (status != NORMAL_COMPLETION)
                {
                        ErrExit("File_To_Message", status);
                }
                a5yntax.setFromString("STREAM_IMPLICIT_LITTLE_ENDIAN");
        } aStatus = encodeDicomList(msgId, fileName, aSyntax);
        if (aStatus != SUCCESS)
        {
                fprintf(stderr, "Schematic-example-code at cmdline %d:
                        %s\n", lineNo, "encodeDicomList() failed");
        }
```

```
    return 0;
} // main
```

Although modifications and changes may be suggested by those skilled in the art, it is the intention of the inventor to embody within the patent warranted hereon all changes and modifications as reasonably and properly come within the scope of his contribution to the art.

Although modifications and changes may be suggested by those skilled in the art, it is the intention of the inventor to embody within the patent warranted hereon all changes and modifications as reasonable and properly come within the scope of his contribution to the art.

I claim as my invention:

1. A medical system architecture comprising:
    at least one imaging modality that acquires medical examination images;
    a computer workstation associated with said at least one imaging modality;
    a data transfer device that transfers data and messages and said medical examination images between at least one client and at least one server;
    a storage device connected to said data transfer device that stores at least said medical examination images;
    at least one further computer workstation connected to said data transfer device configured for post-processing said data and said examination images; and
    a proxy server in communication exclusively with said data transfer device configured to convert said messages between said at least one client and said at least one server according to predetermined transformation rules that make operation of said proxy server transparent to said data transfer device, and thus to said at least one imaging modality, said computer workstation, said storage device and said at least one further computer workstation.

2. A medical system architecture as claimed in claim 1 wherein said data transfer device exchanges said data, examination images and messages according to the DICOM standard.

3. A medical system architecture as claimed in claim 1 comprising a rules memory, accessible by said proxy server, wherein said transformation rules are stored.

4. A medical system architecture as claimed in claim 1 wherein said proxy server comprises a software product separate from said data transfer device.

5. A medical system architecture as claimed in claim 1 wherein said proxy server operates at a same system node as said data transfer device.

6. A medical system architecture as claimed in claim 1 wherein said proxy server operates on a network node.

7. A method for exchanging messages comprising the steps of:
    providing a network comprising a plurality of nodes and a proxy server
    formulating messages at a first of said nodes which are to be transmitted to another of such nodes via said network, each of said messages having a content;
    exchanging said messages between a client and a server connected to said network at respective nodes of said network; and
    in said proxy server, manipulating the respective contents of said messages during transmission of said messages in said network using a computerized conversion routine employing predetermined transformation rules that make said proxy server transparent to all of said notes.

8. A method as claimed in claim 7 comprising formulating said messages according to the DICOM standard.

9. A method as claimed in claim 7 comprising selectively reconfiguring said predetermined transformation rules as needed.

10. A method as claimed in claim 7 comprising storing said predetermined transformation rules in a rules memory, and executing said conversion routine to manipulate the respective contents of the messages in a proxy server having access to said rules memory.

11. A method as claimed in claim 7 wherein said network comprises a plurality of DICOM nodes, and wherein the step of manipulating the respective contents of said messages comprises manipulating the respective contents of said messages in a manner transparent to said DICOM nodes.

* * * * *